(12) United States Patent
Abboud

(10) Patent No.: US 8,720,037 B2
(45) Date of Patent: May 13, 2014

(54) METHOD FOR MAKING A DENTAL GUIDE CHANNEL

(76) Inventor: Marcus Abboud, Setauket, NY (US)

( * ) Notice: Subject to any disclaimer, the term of this patent is extended or adjusted under 35 U.S.C. 154(b) by 0 days.

(21) Appl. No.: 13/432,348

(22) Filed: Mar. 28, 2012

(65) Prior Publication Data

US 2012/0257936 A1    Oct. 11, 2012

(30) Foreign Application Priority Data

Apr. 7, 2011  (DE) .......................... 10 2011 001 888

(51) Int. Cl.
*B23P 13/00*    (2006.01)
*A61C 5/00*    (2006.01)

(52) U.S. Cl.
USPC ............... 29/558; 29/557; 29/896.1; 433/215

(58) Field of Classification Search
USPC ........... 29/26 A, 557, 558, 896.1; 433/72, 75, 433/76, 215
See application file for complete search history.

(56) References Cited

U.S. PATENT DOCUMENTS

| 29,883 A * | 9/1860 | Hathaway ...................... 408/212 |
|---|---|---|
| 132,883 A * | 11/1872 | Whitmore ...................... 408/208 |
| 5,355,574 A * | 10/1994 | Zweekly et al. ................. 29/262 |
| 6,739,872 B1 * | 5/2004 | Turri ................................. 433/75 |
| 8,105,081 B2 * | 1/2012 | Bavar .............................. 433/75 |
| 8,414,296 B2 * | 4/2013 | Berckmans et al. ........... 433/215 |
| 8,419,426 B2 * | 4/2013 | Paris et al. ...................... 433/75 |
| 8,425,227 B2 * | 4/2013 | Marotta ........................... 433/72 |
| 8,439,675 B2 * | 5/2013 | De Moyer ...................... 433/75 |
| 8,529,255 B2 * | 9/2013 | Poirier et al. ................... 433/72 |
| 8,579,628 B2 * | 11/2013 | Drews et al. .................... 433/75 |
| 2006/0093988 A1 * | 5/2006 | Swaelens et al. ............... 433/76 |
| 2009/0011382 A1 * | 1/2009 | Bavar .............................. 433/76 |
| 2009/0191015 A1 * | 7/2009 | Quinn ...................... 408/115 R |
| 2010/0035201 A1 | 2/2010 | Beck et al. |
| 2010/0173259 A1 * | 7/2010 | Vogel et al. .................... 433/72 |
| 2012/0010740 A1 | 1/2012 | Swaelens et al. |
| 2012/0053593 A1 | 3/2012 | Abboud |
| 2012/0123417 A1 * | 5/2012 | Smith .............................. 606/80 |
| 2013/0157219 A1 * | 6/2013 | Lo et al. .......................... 433/76 |
| 2013/0209953 A1 * | 8/2013 | Arlinsky et al. ................ 433/27 |
| 2013/0244205 A1 * | 9/2013 | Berckmans et al. .......... 433/173 |
| 2013/0280673 A1 * | 10/2013 | Maksim .......................... 433/75 |
| 2013/0344453 A1 * | 12/2013 | Eder ............................... 433/29 |

FOREIGN PATENT DOCUMENTS

| EP | 1 596 754 B1 | 11/2005 |
|---|---|---|
| EP | 1 894 539 A1 | 3/2008 |
| EP | 2 246 007 A1 | 11/2010 |
| WO | WO 2010/097 405 A1 | 9/2010 |

* cited by examiner

*Primary Examiner* — Essama Omgba
*Assistant Examiner* — Darrell C Ford
(74) *Attorney, Agent, or Firm* — Norman B. Thot

(57) ABSTRACT

A method for making a guide channel includes providing an auxiliary jig comprising a coupling structure and a corresponding coupling structure of a drilling jig so that the auxiliary jig and the drilling jig are arranged in a defined spatial position. An auxiliary bore is drilled into the auxiliary jig. An auxiliary bore sleeve comprising a reference ring plane is inserted into the auxiliary bore predefined by a target depth. The auxiliary jig is placed on the drilling jig in the defined spatial position. A guide bore is drilled into the drilling jig. A guide sleeve is inserted into the guide bore using a positioning tool so as to form the guide channel. The guide sleeve comprises a depth stop for the drill stop. The guide sleeve is inserted to an insertion depth defined by the reference ring plane and the reference device. The auxiliary jig is removed.

8 Claims, 3 Drawing Sheets

METHOD FOR MAKING A DENTAL GUIDE CHANNEL

CROSS REFERENCE TO PRIOR APPLICATIONS

Priority is claimed to German Patent Application No. DE 10 2011 001 888.3, filed Apr. 7, 2011. The entire disclosure of said application is incorporated by reference herein.

FIELD

The present invention provides a method for making a guide channel in a drilling jig, wherein the drilling jig is used in drilling a dental implant bore in a jaw, intended to be drilled into a patient's jaw bone to a target depth $L_1$.

BACKGROUND

Before a dental implant can be implanted in the jaw bone of a patient, a jaw bore must be drilled into the jaw bone of the patient into which the dental implant is thereafter placed or screwed. It is of critical importance for the cosmetic quality and the durability of the dental prosthesis supported by the dental implant that the spatial position, the orientation and the depth of the implant bore in the jaw are exact with respect to the planning.

For an exact drilling of the jaw bore, a drilling jig is described in WO2010/097405 A1 which comprises an individualized part individually adapted to the respective jaw of a patient, for example, by an impression taken before. The drilling jig can be set on the relevant jaw of a patient in a form-fitting manner and in a manner reproducible with respect to the spatial position and orientation. The drilling jig has a guide channel that is in exact alignment with the planned jaw bore when the drilling jig is set on the patient's jaw. The guide channel serves to guide the jaw drill with which the jaw bore is drilled into the jaw bone.

The guide channel in the drilling jig is formed using an auxiliary jig that can be produced at a location remote from the drilling jig. In producing the auxiliary jig, an auxiliary bore is first drilled into an auxiliary jig body of plastic material into which an auxiliary drilling sleeve of metal is inserted. Both the drilling jig and the auxiliary jig have respective coupling structures that correspond to each other and are complementary to each other, the structures providing for a defined spatial position of the drilling jig and the auxiliary jig coupled thereto. The spatial position and orientation of the auxiliary jig correspond to the spatial position and orientation of the planned jaw bore so that the auxiliary bore and the auxiliary bore sleeve are in exact alignment with the planned jaw bore if the drilling jig were set on the patient's jaw and the auxiliary jig were set on the drilling jig.

Using the auxiliary jig set on the drilling jig, a dentist can use an appropriate drill to drill a guide bore in the plastic drilling jig body, which is aligned with the with the auxiliary bore sleeve. The auxiliary jig is thereafter removed from the drilling jig body, whereupon a metal guide sleeve is inserted, e.g., screwed, into the guide bore. The guide bore forms the guide channel for drilling the jaw bore into the jaw bone.

The finished drilling jig is subsequently set on the patient's jaw. The jaw bore for the dental implant is then drilled into the patient's jaw bone using a jaw drill, the drilling being performed in alignment with the guide sleeve or the guide channel of the drilling jig. The required depth of the jaw bore in the jaw bone is here more or less left to the subjective judgment of the dentist.

SUMMARY

An aspect of the present invention is to provide a method for making a drilling jig that is obtained with the help of an auxiliary jig and is defined by the depth of the jaw bore to be drilled.

In an embodiment, the present invention provides a method for making a guide channel in a drilling jig for drilling a dental implant jaw bore to be bored into a patient's jaw bone to a target depth $L1$ using a jaw drill with a drill stop which includes providing an auxiliary jig comprising a coupling structure which corresponds to a corresponding coupling structure of the drilling jig so that the auxiliary jig and the drilling jig are arranged in a defined spatial position relative to each other. An auxiliary bore is drilled into the auxiliary jig so as to be in a virtual axial alignment with the planned dental implant jaw bore. An auxiliary bore sleeve comprising a reference ring plane is inserted into the auxiliary bore in an axial position predefined by the target depth $L1$ of the planned jaw dental implant jaw bore. The auxiliary jig is placed on the drilling jig in the spatial position defined by the coupling structure and the corresponding coupling structure. A guide bore is drilled into the drilling jig so as to be in axial alignment with the auxiliary bore sleeve. A guide sleeve is inserted into the guide bore using a positioning tool comprising a reference device so as to form the guide channel. The guide sleeve comprises a depth stop for the drill stop. The guide sleeve is inserted to an insertion depth defined by the reference ring plane and the reference device. The auxiliary jig is removed.

BRIEF DESCRIPTION OF THE DRAWINGS

The present invention is described in greater detail below on the basis of embodiments and of the drawings in which.

DETAILED DESCRIPTION

Figure 1:
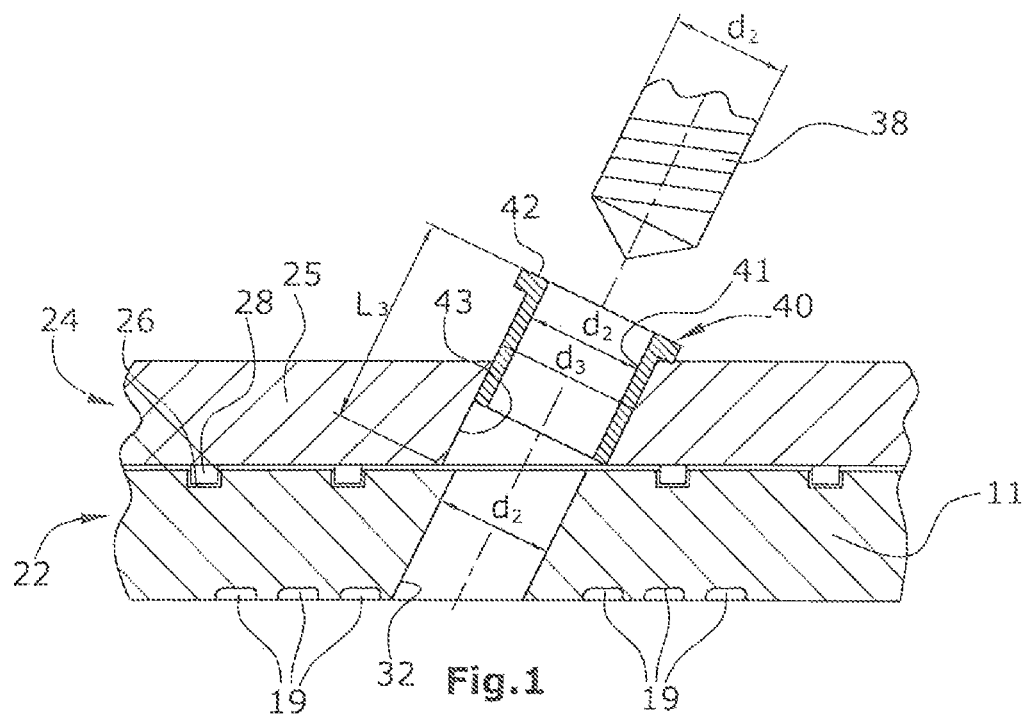
FIG. 1 shows the auxiliary jig set on the drilling jig and a continuous guide bore drilled into the drilling jig body using a guide bore drill.

The method of the present invention provides a drilling jig with a guide channel and a depth stop, so that the jaw bore can be drilled into a patient's jaw bone to a planned target depth $L_1$ using a jaw drill with a drill stop corresponding to the depth stop.

To achieve this, it is provided that first, in a manner known per se, an auxiliary bore is drilled into the auxiliary jig or the auxiliary jig body in virtual axial alignment with the planned jaw bore that has been planned before at a computer with regard to its position, orientation and depth, using a three-dimensional X-ray image of the patient's jaw.

An auxiliary bore sleeve is thereafter inserted, e.g., screwed, into the auxiliary bore in an axial position predetermined by the target depth $L_1$ of the planned jaw bore. The auxiliary bore sleeve has a reference ring plane serving as an axial reference during the following work on the drilling jig. The material of the auxiliary bore sleeve is harder than that of the auxiliary jig body, so that the auxiliary jig sleeve is adapted to guide a drill.

The thus finished auxiliary jig is shipped from the site of production of the auxiliary jig to site where the drilling jig is, e.g., to a dentist or to a dental technician. The auxiliary jig is set on the drilling jig, with the coupling structures of the auxiliary jig and the drilling jig corresponding such that the auxiliary jig and the drilling jig are arranged in a defined and known spatial position with respect to each other. The dentist or the dental technician can thereafter use an appropriate drill, which is guided by the auxiliary bore sleeve of the auxiliary jig, to drill a guide bore into the drilling jig body, which bore is in axial alignment with the auxiliary bore sleeve.

A guide sleeve forming the guide channel is thereafter set into the guide bore, e.g., by screwing. To do this, a positioning tool is used that comprises a reference means which, by referencing to the reference ring plane of the auxiliary bore sleeve, allows for an exact axial positioning of the guide sleeve at a defined insertion depth in the drilling jig body. The positioning tool does not necessarily have to serve for an axial movement of the guide sleeve in the guide bore, but it is always used to control the insertion depth of the guide sleeve in the guide bore. After the guide sleeve in the drilling jig sits in its correct axial position, i.e., at the defined insertion depth, the auxiliary jig, now no longer needed, is removed from the drilling jig.

The drilling jig with its individualized part can thereafter be set on the relevant jaw of a patient. The dentist can now use a jaw drill having an axial drill stop to drill a jaw bore into the jaw bone of the patient. In the process, the jaw drill is guided in the guide channel of the guide sleeve. Upon reaching the target depth $L_1$ of the planned jaw bore, the drill stop of the jaw drill will abut against the depth stop of the guide sleeve, so that the axial depth of the jaw bore is thereby limited to the target depth $L_1$.

The insertion of the auxiliary bore sleeve into the auxiliary jig in an axial position defined by the target depth $L_1$ of the planned jaw bore, the reference ring plane of the auxiliary bore sleeve of the auxiliary jig, the matching coupling structures of the auxiliary jig and the drilling jig, the insertion tool reference means in cooperation with the reference ring plane and the auxiliary sleeve depth stop in cooperation with the drill stop of the jaw drill, a series of axial reference points is created that allows and provides a drilling of the jaw bore to exactly the planned target depth $L_1$.

The reference means of the positioning tool may, for example, be an optically readable depth measuring device which in the simplest case is a mere marker that has to be made flush with the reference ring plane of the auxiliary bore sleeve. However, a measuring device that can be read only in an optical manner caries the inherent danger of erroneous operation and resulting inaccuracies.

In an embodiment of the present invention, the reference means can, for example, be a mechanical tool stop of the positioning tool which cooperates with the reference ring plane of the auxiliary bore sleeve such that the actual insertion depth of the guide sleeve in the drilling jig body exactly corresponds to the planned insertion depth.

In an embodiment of the present invention, the guide sleeve can, for example, have a screw thread on its outer side so that the guide sleeve can be screwed into the auxiliary jig body by turning. For this purpose, the positioning tool has a form fitting structure corresponding to a form fitting structure of the guide sleeve such that the guide sleeve can be turned, i.e., screwed, by means of the positioning tool. If the positioning tool has a mechanical tool stop as the reference means, the same will abut against the reference ring plane upon reaching the target insertion depth, so that in the event of a further screwing of the guide sleeve the engagement of the form fitting structure of the positioning tool with the form fitting structure of the guide sleeve is lost.

In an embodiment of the method of the present invention, the axial position of the guide sleeve in the drilling jig body is not defined by means of a separate positioning tool. The guide bore is rather drilled into the drilling jig using a blind hole drill, the depth of the blind hole or the axial position of the blind hole bottom defining the axial position of the guide sleeve in the guide bore. The blind hole drill has a stop ring surface as the reference means, which abuts against the reference ring plane of the auxiliary bore sleeve of the auxiliary jig when, while drilling the guide bore or the blind hole, the blind hole depth defined by the jaw bore target depth $L_1$ is reached. In this manner, the blind hole depth can be set to a desired value that directly depends on the jaw bore target depth $L_1$.

After the guide bore in the form of a blind hole has been drilled to the defined blind hole depth, the guide sleeve is inserted into the guide bore down to the blind bore bottom, e.g., screwed thereinto, using a screw driver. For this purpose, the guide sleeve may be provided with a screw thread on the outer side.

The following is a detailed description of two embodiments of the present method with reference to the Figures.

Before the making of a drilling jig can begin, a three-dimensional image of the patient's jaw 20 is first made using an X-ray apparatus, e.g., a so-called DVT apparatus. Here, a drilling jig body 11 of plastic material can, for example, be set with an individualized part matching the patient's jaw 20, which may have tooth recesses 19 complementary to the patient's teeth 18, on the patient's jaw 20. The drilling jig body 11 has removable and radiologically opaque X-ray markers that are not illustrated in the Figures. The X-ray markers provide the spatial relationship between the drilling jig body 11, the image of the patient's jaw and the patient's jaw 20.

In the three-dimensional image of the patient's jaw, a dental implant is planned that is intended to support an artificial tooth structure in the future. The position of the dental implant in the patient's jaw 20 also defines the position, orientation and target depth $L_1$ of the jaw bore 10 for the dental implant. The information about the spatial position, orientation and target depth $L_1$ of the jaw bore are transmitted to a site where the auxiliary jig is manufactured.

At the auxiliary jig manufacturing site, only an auxiliary jig 24 is made, but no work is done on the drilling jig 22 which can remain at the treatment site. The auxiliary jig 24 and the drilling jig 22 each have a standardized and complementary coupling structure 28, 26 by which the auxiliary jig 24 and the drilling jig 22 or the auxiliary jig body 25 and the drilling jig body 11 can be joined in a known and reproducible spatial position relative to each other.

Using the information about the position, orientation and target depth $L_1$ of the planned jaw bore 10, transmitted to the auxiliary jig manufacturing site, an auxiliary bore 43 with an outer diameter $d_3$ is drilled into the auxiliary jig body 25 by means of a digitally controlled drill apparatus, such that the auxiliary bore 43 would be in axial alignment with the planned jaw bore if the auxiliary jig 24 were set on the drilling jig 22 and the drilling jig 22 were set on the on the patient's jaw 20. A metal auxiliary bore sleeve 40 with an auxiliary guide channel 41 is thereafter set into the auxiliary bore 43, e.g., by screwing. To this effect, the auxiliary bore sleeve 40 can, for example, have a low pitch screw thread on its outer side. The substantially cylindrical auxiliary bore sleeve 40 is inserted into the auxiliary jig body 25 in an axial position defined by the target depth $L_1$ of the planned jaw bore 10 and is fixed in that axial position, e.g., by gluing. At its distal longitudinal end, i.e., the longitudinal end facing away from the drilling jig 22, the auxiliary bore sleeve 40 has a reference ring plane 42 serving as an axial reference during the subsequent forming of the guide channel in the drilling jig 22. The auxiliary jig 24 thus manufactured is then shipped to the treatment site.

At the treatment site, the auxiliary jig 24 is set on the drilling jig 22, the spatial position of the auxiliary jig 24 relative to the drilling jig 22 being clearly defined by the respective coupling structures 26, 28. This situation is illustrated in FIG. 1. Using a guide bore drill 38 with an outer diameter $d_2$ that corresponds to the inner diameter $d_2$ of the auxiliary bore sleeve 40, a continuous guide bore 32 is drilled manually into the drilling jig body 11. The drill 38 is then removed.

A metal guide sleeve 30 is thereafter screwed into the guide bore 32. The guide sleeve 30 has a screw thread 31 on its outer side, an outer diameter $d_2$ and an inner diameter $d_1$. The inside of the guide sleeve 30 forms the guide channel 12 for guiding the jaw drill 80 in drilling the jaw bore 10. The inner diameter $d_1$ of the guide channel 12 corresponds to the inner diameter $d_1$ of the planned jaw bore 10. At the longitudinal end facing the auxiliary jig 24, the guide sleeve 30 comprises a form fitting structure 35 in form of a cross recess. The longitudinal end facing the auxiliary jig 24 lies exactly in a transversal plane and forms a depth stop 34 for a drill stop 84 of the jaw drill 80.

Figure 2:
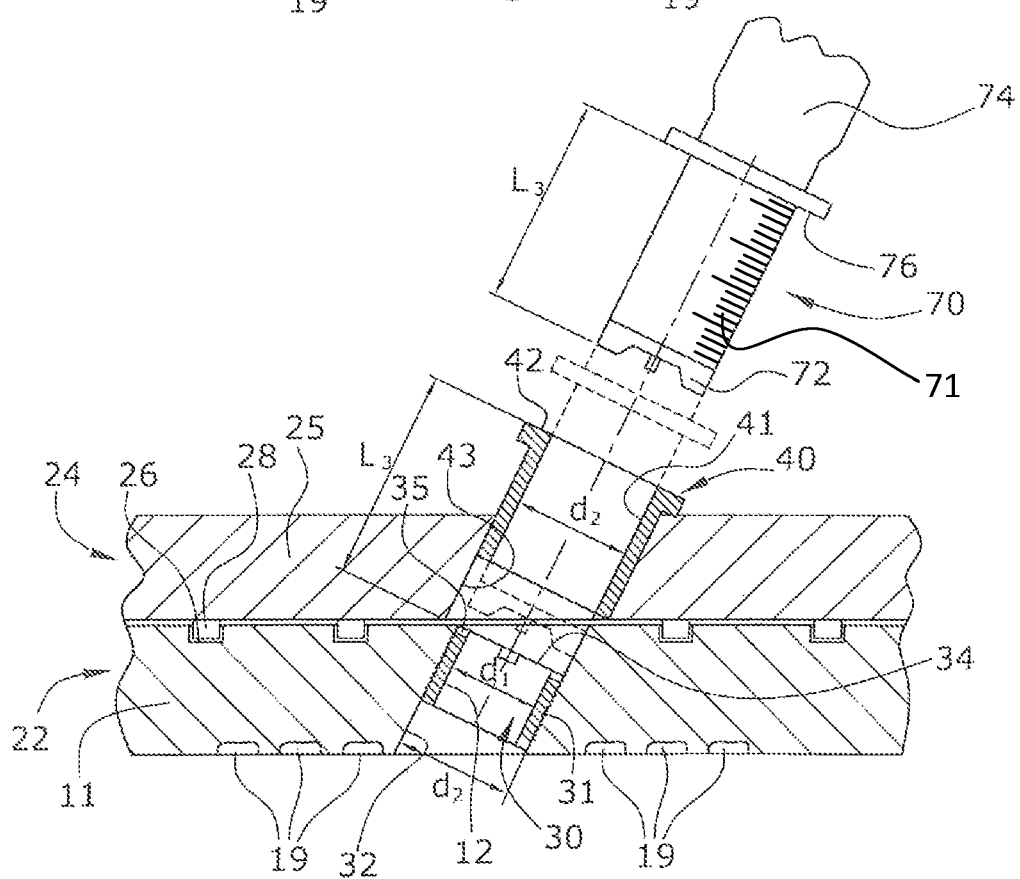
FIG. 2 shows the guide sleeve screwed into the guide bore using a positioning tool with which the guide sleeve can be screwed into the drilling jig body to a defined depth.

As can be seen in FIG. 2, the guide sleeve 30 is screwed into the guide bore 32 using a positioning tool 70 with which the guide sleeve 30 can be screwed into the drilling jig body 11 to a defined depth. The positioning tool 70 has a handle 74 at one longitudinal end, a cross-shaped form fitting structure 72 at the other longitudinal end and, in between, a ring surface 76 as a reference means 76 which is spaced by a known axial insertion distance $L_3$ from the form fitting structure 72. The reference means 76 of the positioning tool also has an optically readable depth measuring device 71 which in the shown embodiment is a mere marker.

The form fitting structure 72 of the positioning tool 70 is set to the form fitting structure 35 of the guide sleeve 30 and the guide sleeve 30 is screwed into the guide bore 32 using the positioning tool 70. In the process, the depth stop 34 of the guide sleeve 30 progressively moves away in the axial direction from the reference ring plane 42 of the auxiliary bore sleeve 40, until the reference means 76 of the positioning tool 70 abuts against the reference ring plane 42 of the auxiliary bore sleeve 40. As soon as this happens, the positioning tool 70 cannot be inserted any further into the auxiliary bore sleeve 40 in the axial direction, so that upon a continued screwing movement, the form fitting structures 72, 35 of the positioning tool 70 and of the guide sleeve 30 disengage. When this happens, the insertion distance $L_3$ between the reference ring plane 42 of the auxiliary bore sleeve 40 and the depth stop 34 of the guide sleeve 30 is reached, and the positioning tool 70 and the auxiliary jig 24 can be removed from the drilling jig 22. It is possible to fix the guide sleeve 30 against rotation, e.g., by gluing. The drilling jig 22 is now finished.

Figure 3:
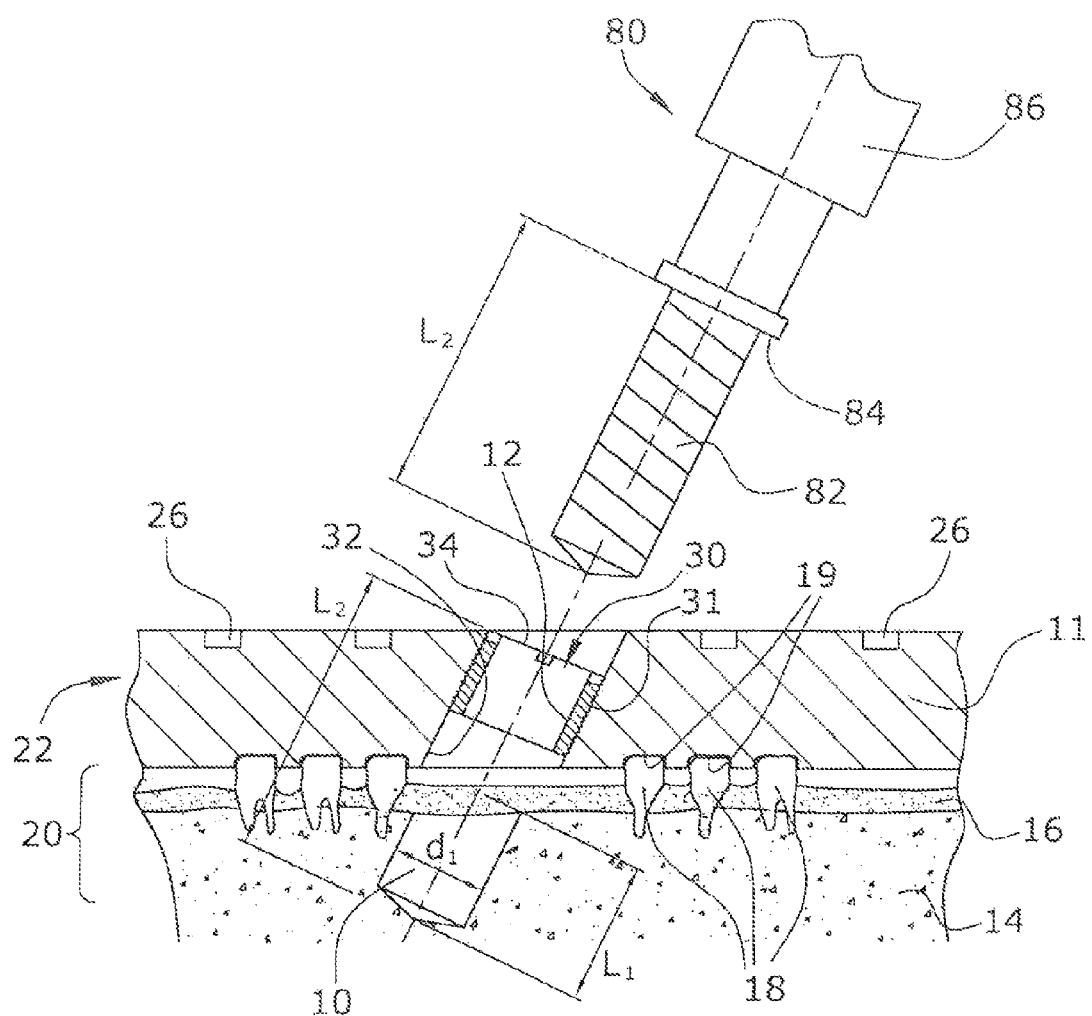
FIG. 3 shows the drilling jig set on the patient's jaw in a form fitting manner so that the jaw bore can thereafter be drilled into the jaw bone of the patient's jaw using the jaw drill.

As illustrated in FIG. 3, the drilling jig 22 is then set on the patient's jaw 20 in a form fitting manner. The jaw bore 10 is thereafter drilled into the jaw bone 14 of the patient's jaw 20, using the jaw drill 80. The jaw drill 80 has a handle 86, a drill shaft 82 and a drill stop 84 in the form of a ring surface. The drill stop 84 is spaced axially from the distal end or the tip of the drill shaft 82 by the drilling length $L_2$. The depth of the bore in the patient's jaw 20 is limited to the known drilling length $L_2$ by the drill stop 84 on the one hand and the depth stop 34 of the guide sleeve 30 on the other hand, so that also the axial depth of the jaw bore 10 is thus limited or set exactly to its target depth $L_1$.

In the above described manufacturing of the auxiliary jig 24, the auxiliary bore sleeve 40 is positioned axially such that the known and predetermined axial measures $L_2$ and $L_3$ necessarily result in the target depth $L_1$ when drilling the jaw bore 10.

Figure 4:
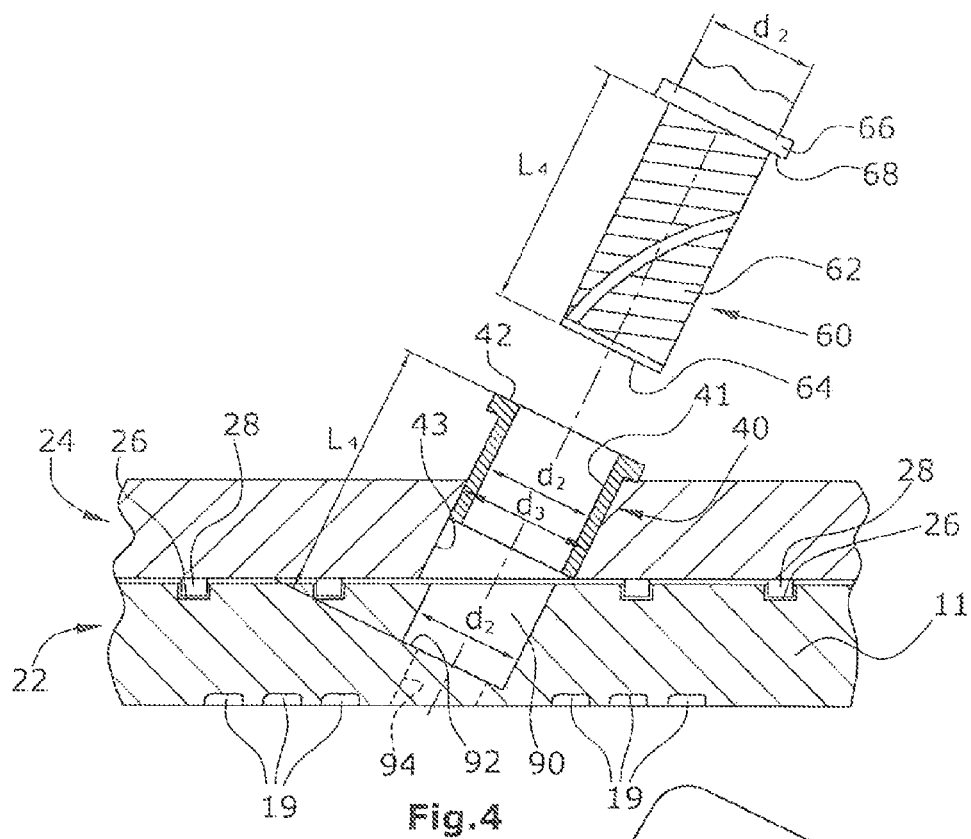
FIG. 4. shows an embodiment where the blind hole is drilled into the drilling jig body using the blind hole drill with the drill shaft guided in the auxiliary guide channel of the auxiliary guide sleeve.
Figure 5:
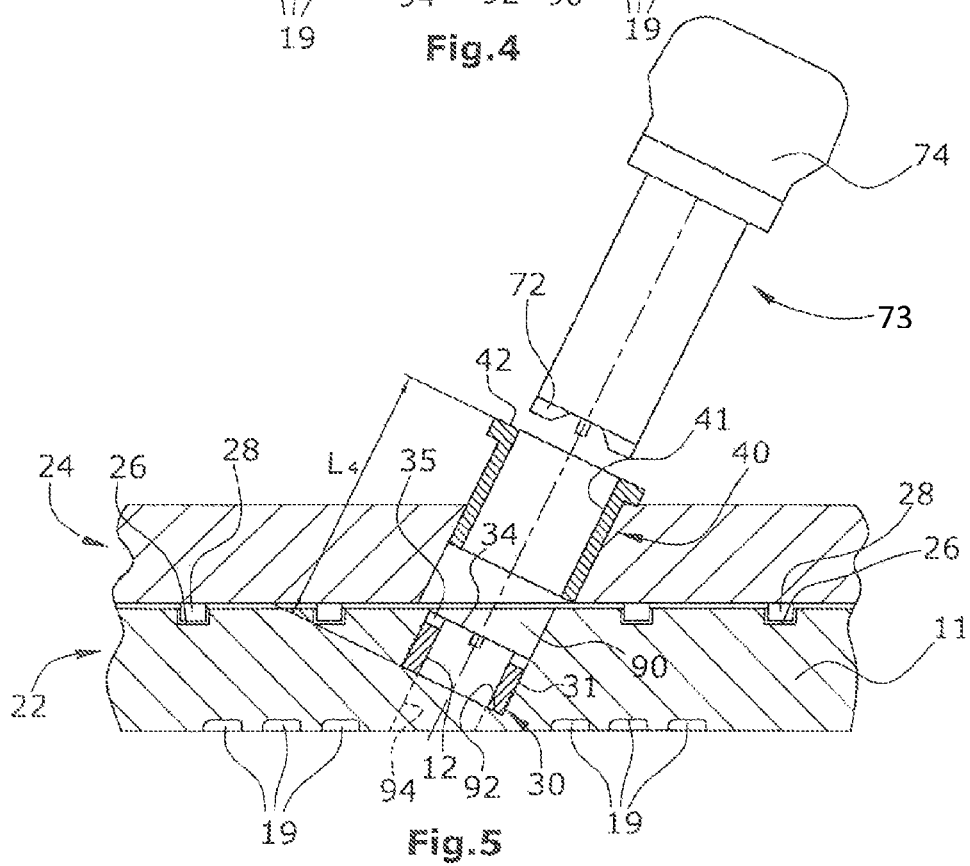
FIGS. 5 shows an embodiment where the guide sleeve has been screwed into the blind hole bore using a screw driving tool.

FIGS. 4 and 5 illustrate a second, alternative embodiment of the above described method, with the manufacturing of the auxiliary jig 24 and the last method step illustrated in FIG. 3 being virtually identical. In the method shown in FIGS. 4 and 5, other than in the method steps illustrated in FIGS. 1 and 2, the axial position of the guide sleeve 30 is defined by the blind hole depth of a blind hole bore 90 in the drilling jig body 11. As illustrated in FIG. 4, a blind hole drill 60 with a drill shaft 62, a stop ring 66 with a stop ring surface 68 and face cutting edges 64 lying in a transversal plane and arranged at the face end is used for that. The outer diameter $d_2$ of the drill shaft 62 approximately corresponds to the inner diameter $d_2$ of the auxiliary bore sleeve 40. The drill shaft length $L_4$ is known and is defined by the axial distance between the stop ring surface 68 and the face cutting edges 64. With the drill shaft 62 guided in the auxiliary guide channel 41 of the auxiliary guide sleeve 40, the blind hole 90 is drilled into the drilling jig body 11 using the blind hole drill 60. The depth of the blind hole 90 or the axial position of the blind hole bottom 92 is defined by the known drill shaft length $L_4$ and the fixed axial position of the reference ring plane 42 of the auxiliary bore sleeve 40.

After having drilled the blind hole 90, the blind hole drill 60 and the auxiliary jig 24 are removed from the drilling jig 22. As illustrated in FIG. 5, the guide sleeve 30 is then screwed into the blind hole bore 90 using a screw driving tool 73. For this purpose, the screw driving tool 73 has a form fitting structure 72 at its distal end, which cooperates with the complementary form fitting structure 35 of the guide sleeve 30. The guide sleeve 30 is screwed into the blind hole bore 90 until the front end face of the guide sleeve 30 abuts against the blind hole bottom 92. In this position the guide sleeve 30 is in a defined axial position, in which the distance of the front end face of the guide sleeve 30 to the reference ring plane 42 of the auxiliary bore sleeve 40 corresponds exactly to the drill shaft length $L_4$ of the blind hole drill 60.

The screw driving tool 73 and the auxiliary jig 24 can thereafter be removed from the drilling jig 22 and the drilling jig 22 can be set on the patient's jaw 20, as illustrated in FIG. 3. When drilling the jaw bore 10, the jaw drill 80 first drills through the blind hole bottom 92, so that a connection channel 94 adjoins the guide channel 12 of the guide sleeve 30, the inner diameter of the connection channel being approximately equal to the outer diameter of the jaw drill 80.

The present invention is not limited to embodiments described herein; reference should be had to the appended claims.

What is claimed is:

1. A method for making a guide channel in a drilling jig for drilling a dental implant jaw bore to be bored into a patient's jaw bone to a target depth (L1) using a jaw drill with a drill stop, the method comprising:

step 1 providing an auxiliary jig comprising a coupling structure which corresponds to a corresponding coupling structure of the drilling jig so that the auxiliary jig and the drilling jig are arranged in a defined spatial position relative to each other;

step 2 drilling an auxiliary bore into the auxiliary jig so as to be in a virtual axial alignment with the planned dental implant jaw bore;

step 3 inserting an auxiliary bore sleeve comprising a reference ring plane into the auxiliary bore in an axial position predefined by the target depth (L1) of the planned jaw dental implant jaw bore;

step 4 placing the auxiliary jig on the drilling jig in the spatial position defined by the coupling structure and the corresponding coupling structure;

step 5 drilling a guide bore into the drilling jig so as to be in axial alignment with the auxiliary bore sleeve;

step 6 inserting a guide sleeve into the guide bore using a positioning tool comprising a reference device so as to form the guide channel, the guide sleeve comprising a depth stop for the drill stop, the guide sleeve being inserted to an insertion depth defined by the reference ring plane and the reference device; and step 7 removing the auxiliary jig, wherein, steps 1-7 are performed in the order set forth.

2. The method as recited in claim 1, wherein the positioning tool comprises a mechanical tool stop as the reference device, the mechanical tool stop being configured to cooperate with the reference ring plane.

3. The method as recited in claim 1, wherein the positioning tool comprises a depth measuring device as the reference device.

4. The method as recited in claim 1, wherein the positioning tool comprises a form fitting structure, and the guide sleeve comprises a screw thread on an outer side and a corresponding form fitting structure, wherein the form fitting structure of the positioning tool is configured to cooperate with the corresponding form fitting structure of the guide sleeve.

5. A method for making a guide channel in a drilling jig for drilling a dental implant jaw bore to be bored into a patient's jaw bone to a target depth (L1) using a jaw drill with a drill stop, the method comprising:

step 1 providing an auxiliary jig comprising a coupling structure which corresponds to a corresponding coupling structure of the drilling jig so that the auxiliary jig and the drilling jig are arranged in a defined spatial position relative to each other;

step 2 drilling an auxiliary bore into the auxiliary jig so as to be in a virtual axial alignment with the planned dental implant jaw bore;

step 3 inserting an auxiliary bore sleeve comprising a reference ring plane into the auxiliary bore in an axial position predefined by the target depth (L1) of the planned jaw dental implant jaw bore;

step 4 placing the auxiliary jig on the drilling jig in the spatial position defined by the coupling structure and the corresponding coupling structure;

step 5 drilling a guide bore into the drilling jig so as to be in axial alignment with the auxiliary bore sleeve using a blind hole drill comprising a blind hole drill stop ring surface as a reference device, which together with the reference ring surface defines a blind hole depth;

step 6 inserting a guide sleeve so as to form the guide channel, the guide sleeve comprising a depth stop for the drill stop, into the guide bore to an insertion depth defined by the blind hole depth; and step 7 removing the auxiliary jig, wherein, steps 1-7 are performed in the order set forth.

6. The method as recited in claim 5, wherein the positioning tool comprises a mechanical tool stop as the reference device, the mechanical tool stop being configured to cooperate with the reference ring plane.

7. The method as recited in claim 5, wherein the positioning tool comprises a depth measuring device as the reference device.

8. The method as recited in claim 5, wherein the positioning tool comprises a form fitting structure, and the guide sleeve comprises a screw thread on an outer side and a corresponding form fitting structure, wherein the form fitting structure of the positioning tool is configured to cooperate with the corresponding form fitting structure of the guide sleeve.

* * * * *